(12) United States Patent
Uthgenannt (10) Patent No.: US 9,463,030 B2
(45) Date of Patent: Oct. 11, 2016

(54) POSITIONING MULTIPLE IMPLANTS WITH RESPECT TO SINGLE COORDINATE SYSTEM

(71) Applicant: Biomet Manufacturing, LLC, Warsaw, IN (US)

(72) Inventor: Brian Uthgenannt, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 311 days.

(21) Appl. No.: 14/036,124

(22) Filed: Sep. 25, 2013

(65) Prior Publication Data

US 2015/0088141 A1    Mar. 26, 2015

(51) Int. Cl.
| | | |
|---|---|---|
| A61B 17/16 | (2006.01) | |
| A61F 2/38 | (2006.01) | |
| A61F 2/46 | (2006.01) | |
| A61B 17/15 | (2006.01) | |
| A61B 17/56 | (2006.01) | |

(52) U.S. Cl.
CPC ......... *A61B 17/1675* (2013.01); *A61B 17/155* (2013.01); *A61B 17/157* (2013.01); *A61B 34/20* (2016.02); *A61F 2/38* (2013.01); *A61F 2/4684* (2013.01); *A61B 2017/568* (2013.01); *A61F 2/389* (2013.01); *A61F 2002/4666* (2013.01)

(58) Field of Classification Search
CPC ...... A61B 17/16; A61B 17/1675; A61F 2/38
USPC ................... 606/79, 80, 86 R, 87, 88, 96–98; 623/20.14
See application file for complete search history.

(56) References Cited

U.S. PATENT DOCUMENTS

| | | | |
|---|---|---|---|
| 7,780,672 B2 | 8/2010 | Metzger et al. | |
| 8,070,752 B2 | 12/2011 | Metzger et al. | |
| 8,092,465 B2 | 1/2012 | Metzger et al. | |
| 8,298,237 B2 | 10/2012 | Schoenefeld et al. | |
| 8,608,748 B2 | 12/2013 | Metzger et al. | |
| 2003/0212403 A1* | 11/2003 | Swanson ............... | A61B 17/155 606/88 |
| 2013/0190767 A1* | 7/2013 | Park ...................... | A61B 17/154 606/87 |
| 2014/0276862 A1* | 9/2014 | Stein .................... | A61B 5/4571 606/88 |

OTHER PUBLICATIONS eLIBRA® Dynamic Knee Balancing System—Optimum Flexion Gap and Ligament Balance (Zimmer and Synvasive® Technology, Inc.) (4 pages).

(Continued)

*Primary Examiner* — Christopher Beccia
(74) *Attorney, Agent, or Firm* — Schwegman Lundberg & Woessner, P.A.

(57) ABSTRACT

A method for preparing a femur and a tibia to receive implants. The method includes mapping location of a femoral guide to a coordinate system using a femoral position sensor mounted to at least one of the femoral guide or another femoral surgical device during preparation of the femur to receive a femoral implant. The method further includes mapping location of a tibial guide to the coordinate system using a tibial position sensor mounted to at least one of the tibial guide or another tibial surgical device during preparation of the tibia to receive a tibial implant.

20 Claims, 5 Drawing Sheets

(56) References Cited

OTHER PUBLICATIONS

OrthAlign Products and Technology May 23, 2013—www.orthalign.com/products_technology/kneealign.asp; www.orthalign.com/products_technology/how_it_works.asp; www.orthalign.com/products_technology/components.asp; www.orthalign.com/surgeons/default.asp; www.orthalign.com/surgeons/features_benefits.asp (6 pages).

OrthoSensor Surgical Instruments, Implantables, Analytics, and Technology May 23, 2013—www.orthosensor.com/products/orthosensor-surgical; www.orthosensor.com/products/orthosensor-implantables; www.orthosensor.com/products/orthosensor-analytics; www.orthosensor.com/technology (5 pages).

Praxim Smart Instruments, Basic Instrument Set, Minimally Invasive Fixations, Nanoblock®, and iBlock® Apr. 29, 2013—www.praxim.fr/Products (4 pages).

Synvasive® Technology, Inc. (www.synvasive.com)—eLIBRA® Dynamic Knee Balancing System, *Surgical Technique & System Overview* (14 pages).

* cited by examiner

FIG - 7

POSITIONING MULTIPLE IMPLANTS WITH RESPECT TO SINGLE COORDINATE SYSTEM

FIELD

The present disclosure relates to methods and devices for preparing a femur and a tibia to receive an implant.

BACKGROUND

This section provides background information related to the present disclosure, and is not necessarily prior art. During knee surgery, such as total knee arthroplasty, the femur and tibia are prepared to each receive an implant at a position and orientation best suited to the patient's anatomy, so as to provide the patient with maximum range of motion and comfort post-surgery. Various devices and methods exist to facilitate alignment of tibial and femoral implants, and are subject to improvement.

SUMMARY

This section provides a general summary of the disclosure, and is not a comprehensive disclosure of its full scope or all of its features.

The present teachings provide for a method for preparing a femur and a tibia to receive implants. The method includes mapping location of a femoral guide to a coordinate system using a femoral position sensor mounted to at least one of the femoral guide or another femoral surgical device during preparation of the femur to receive a femoral implant. The method further includes mapping location of a tibial guide to the coordinate system using a tibial position sensor mounted to at least one of the tibial guide or another tibial surgical device during preparation of the tibia to receive a tibial implant.

The present teachings further provide for a method for preparing a femur and a tibia to receive implants. The method includes mapping location of a femoral guide to a leg mechanical axis using a femoral position sensor mounted to at least one of the femoral guide or another femoral surgical device during preparation of the femur to receive a femoral implant at a position relative to the mechanical axis. The method further includes determining a tibial mechanical axis and mounting a tibial guide to the tibia relative to the leg mechanical axis and the tibial mechanical axis using a tibial position sensor mounted to at least one of the tibial resection guide or another tibial surgical device during preparation of the tibia to receive a tibial implant.

The present teachings also include a kit for preparing a femur and a tibia to receive implants. The kit includes a femoral position sensor configured to map location of a femoral guide to a coordinate system. The femoral position sensor is mounted to at least one of the femoral guide or another femoral surgical device for preparing the femur to receive a femoral implant. The kit also includes a tibial position sensor configured to map location of a tibial guide to the coordinate system. The tibial position sensor is mounted to at least one of the tibial guide or another tibial surgical device for preparing the tibia to receive a tibial implant.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
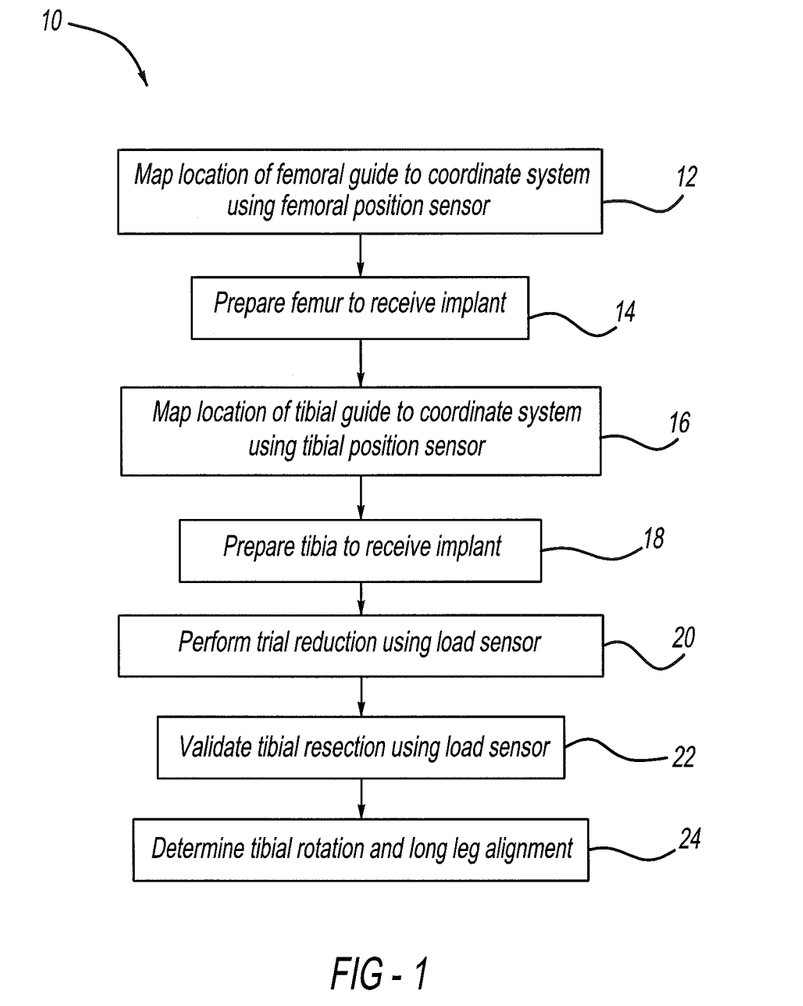
FIG. 1 illustrates a method according to the present teachings for preparing a femur and a tibia to each receive an implant.

With initial reference to FIG. 1, a method according to the present teachings for preparing a femur and a tibia to each receive an implant, such as during a total knee arthroplasty, is generally illustrated at reference numeral 10. As set forth at block 12, to prepare the femur the location of a femoral guide is mapped to a coordinate system using a femoral position sensor. The coordinate system may be any suitable coordinate system of a patient's leg, such as leg mechanical axis A illustrated in FIGS. 2A and 2B. The mechanical axis A extends from femur 50 to tibia 52. More specifically, the leg mechanical axis A extends through a center of head 54 of the femur 50 to a center of a patient's ankle opposite to distal end 56 of the tibia 52.

Figure 3:
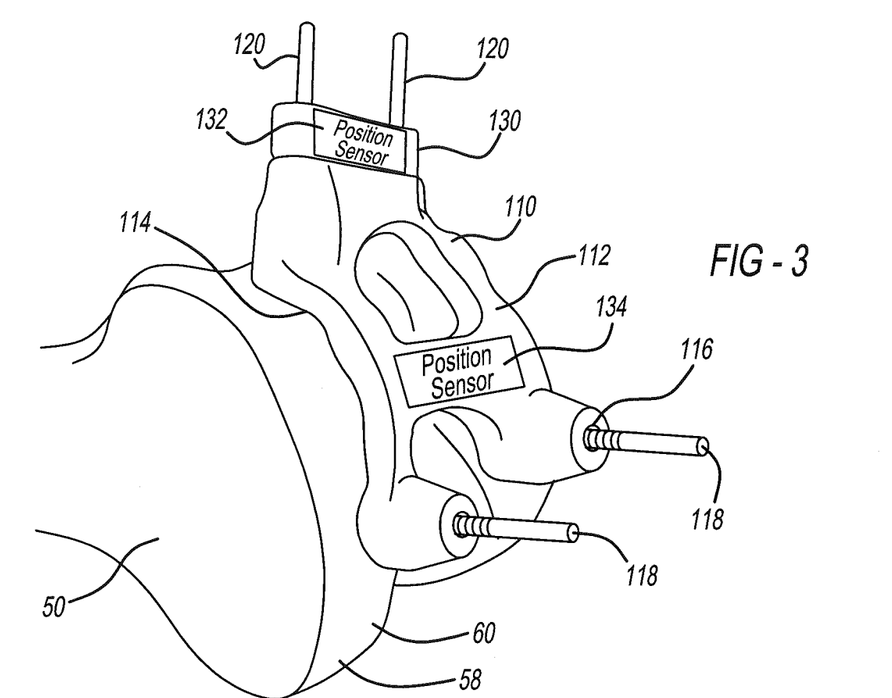
FIG. 3 is a perspective view of a femoral positioning guide according to the present teachings mounted to a femur.
Figure 4:
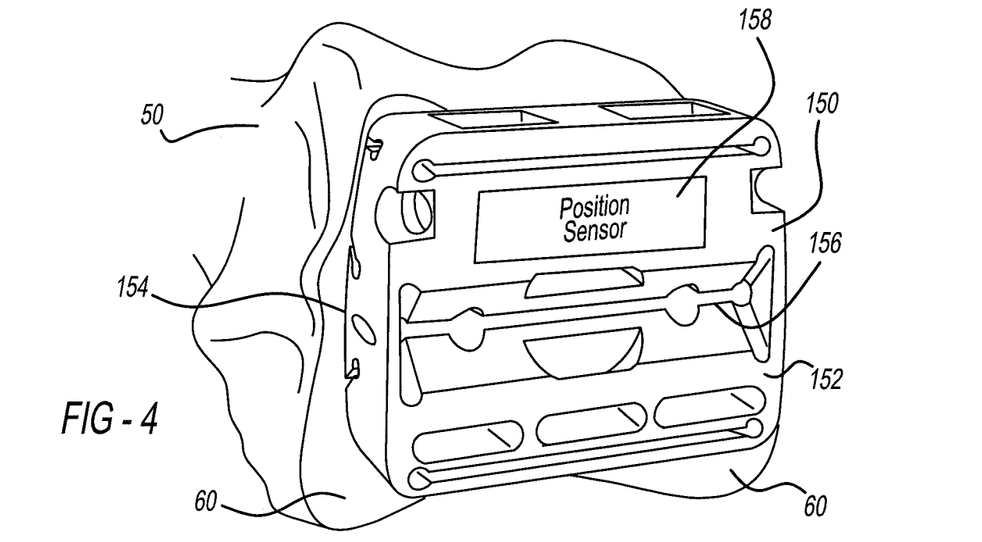
FIG. 4 is a perspective view of a femoral cutting guide according to the present teachings mounted to a femur.

The femoral guide can be any suitable femoral guide, such as femoral positioning guide 110 illustrated in FIG. 3, or femoral cutting guide 150 illustrated in FIG. 4. The femoral positioning guide 110 generally includes an outer surface 112 and a bone-engaging surface 114 opposite thereto. The bone-engaging surface 114 can be a patient-generic surface configured to generally fit a plurality of difference patients. The bone-engaging surface 114 can also be a patient-specific surface configured to couple with a specific patient's bone at only a single location and orientation. When the bone-engaging surface 114 is a patient-specific surface, it will mirror the patient's femur 50 at distal end 58 thereof, including at least a portion of the patient's condyles 60. The patient-specific bone-engaging surface 114 can be based on any suitable imaging of the patient's femur 50, such as three-dimensional imaging including a CAT scan or MRI imaging. Various femoral guides including exemplary patient-specific surfaces are described in the following applications, for example, which are incorporated herein by reference: U.S. patent application Ser. No. 11/756,057, filed on May 31, 2007; U.S. patent application Ser. No. 12/211,407, filed on Sep. 16, 2008; U.S. patent application Ser. No. 11/971,390, filed on Jan. 9, 2008; U.S. patent application Ser. No. 11/363,548, filed on Feb. 27, 2006; and U.S. patent application Ser. No. 12/025,414, filed on Feb. 4, 2008.

With continued reference to FIG. 3, the femoral positioning guide 110 defines distal guide holes 116 extending from the outer surface 112 to the bone-engaging surface 114. The distal guide holes 116 are configured to receive guide distal pins 118 therethrough and guide the distal pins 118 to the femur 50. The femoral positioning guide 110 further includes anterior guide holes (not specifically illustrated) configured to guide anterior pins 120 to the femur 50. The anterior pins 120 extend through drill guide or taper guide 130, which is a femoral surgical device. The drill guide 130 can be coupled to the femoral positioning guide 110 at the anterior guide holes in any suitable manner, such as with a taper fit. The anterior pins 120 are drilled into the femur 50 to form holes therein. The distal pins 118 and the anterior pins 120 can each be any type of pin suitable for securing the femoral positioning guide 110 to the femur 50.

A position sensor 132 can be mounted to, or be integral with, the drill guide 130. Another position sensor 134 can be mounted directly to, or be integral with, the femoral positioning guide 110. Both of the position sensors 132 and 134 can be included, or only one of the position sensors 132 and 134 can be included. The position sensors 132 and 134 can be any suitable position sensors for identifying and mapping the location of the drill guide 130 and/or the femoral positioning guide 110 relative to a coordinate system, such as the mechanical axis A. Location of the position sensor 134 will directly map the position of the femoral positioning guide 110 relative to the mechanical axis A. The position of the femoral positioning guide 110 can be indirectly determined and mapped relative to the mechanical axis A based on the position of the drill guide 130 because the drill guide 130 is rigidly coupled to the femoral positioning guide 110 at a known orientation.

After the distal pins 118 and the anterior pins 120 have been set and corresponding pin holes in the femur 50 have been formed, the distal pins 118 can be removed and the femoral positioning guide 110 can be removed from the femur 50 by sliding it over the anterior pins 120. A distal femoral box cutting guide, which is a femoral guide, can then be slid onto the anterior pins to make distal cuts in the femur 50. The distal femoral box cutting guide may also include a position sensor, such as position sensor 158 described herein mounted to femoral cutting guide 150, which is configured to map location of the distal femoral box cutting guide to the coordinate system, such as the mechanical axis A.

With reference to FIG. 4, after the distal cuts in the femur 50 have been made, the femoral cutting guide 150 may be secured to the femur 50, such as by the distal pins 118 or any other suitable pins extending into the holes formed in the femur 50 when the distal pins 118 were driven therein. The femoral cutting guide 150 generally includes an outer surface 152 and an inner bone-engaging surface 154, which is opposite to the outer surface 152. The femoral cutting guide 150 defines cutting slots 156, which extend from the outer surface 152 to the bone-engaging surface 154. The cutting slots 156 can be configured in any suitable manner to direct a cutting instrument to the femur 50 to make cuts therein to accommodate a femoral implant. The femoral cutting guide 150 can be any suitable cutting guide, such as a four-in-one cutting guide as illustrated in FIG. 4.

The femoral cutting guide 150 further includes a position sensor 158. Like the position sensors 132 and 134, the position sensor 158 can be any suitable position sensor configured to identify and map location of the femoral cutting guide 150 to a coordinate system, such as the mechanical axis A. The distal femoral cuts and the cuts made using the femoral cutting guide 150 prepare the femur 50 to receive an implant, as set forth at block 14 of the method 10.

Mapping the positions of the drill guide 130, the femoral positioning guide 110, the distal femoral box cutting guide, and/or the femoral cutting guide 150 to the mechanical axis A using position sensors 132, 134, and/or 158 respectively will indirectly map orientation of the femoral implant to the mechanical axis A, which will facilitate positioning of the tibial implant so as to best mate with the femoral implant. The positions of the drill guide 130, the femoral positioning guide 110, the drill guides such as the drill guide 130 or the distal femoral box cutting guide, and/or the femoral cutting guide 150 will determine where the cuts for the femoral implant will be made, and thus determine the ultimate location and orientation of the femoral implant relative to the mechanical axis A.

Figures 2A, 2B:
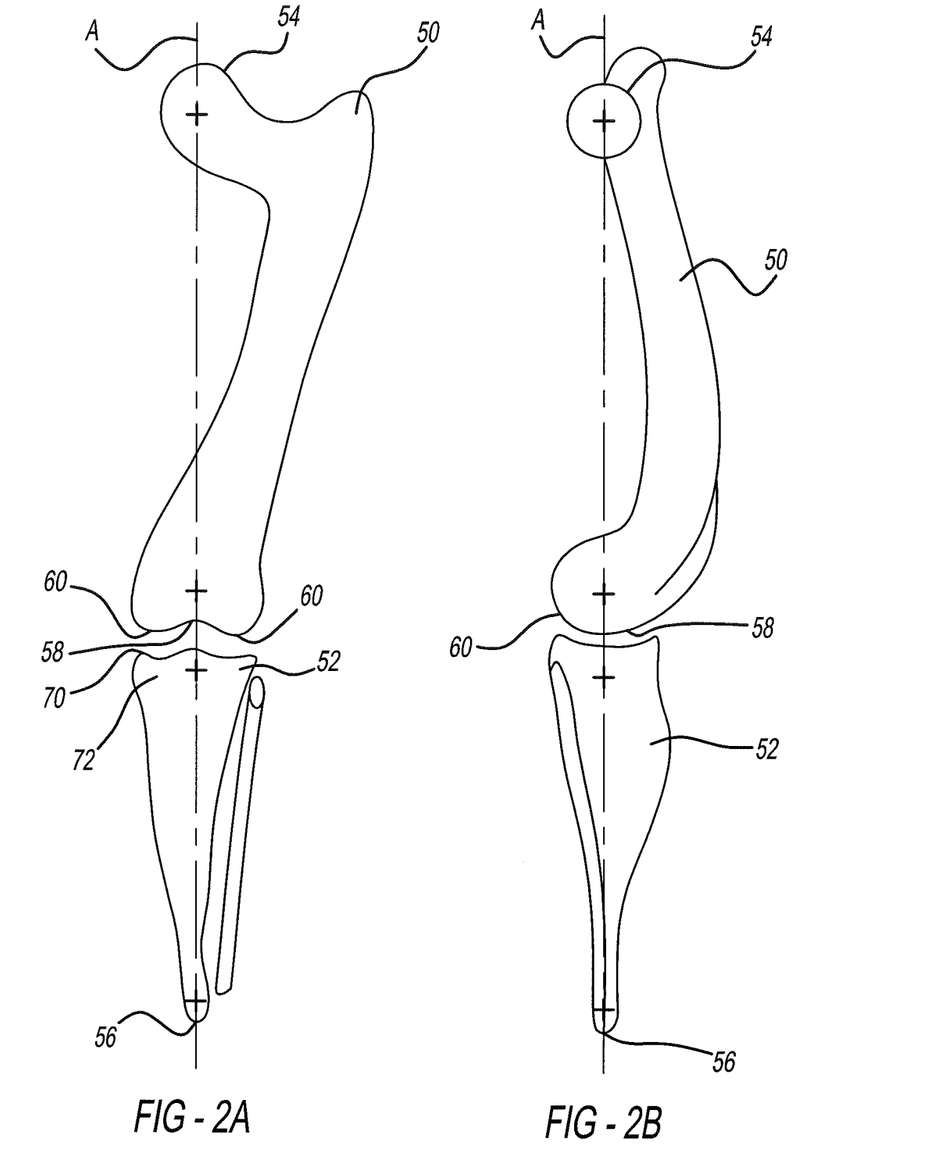
FIG. 2A illustrates a mechanical leg axis viewed along a coronal plane.
FIG. 2B illustrates the mechanical leg axis of FIG. 2A viewed along a sagittal plane.

At block 16 of the method 10 for preparing a femur and tibia to receive an implant, location of a tibial guide is mapped to a coordinate system, such as the mechanical axis A of FIGS. 2A and 2B, using a tibial positioning sensor. For example and with reference to FIG. 5, the tibial guide can be a tibial positioning guide 210 configured to couple to tibia 52 at proximal surface 70, which can be at the tibial plateau, and anterior surface 72. The tibial positioning guide 210 includes an outer surface 212 and an inner or bone-engaging surface 214, which is opposite to the outer surface 212. The bone-engaging surface 214 can be generic to a plurality of different patients, or can be a patient-specific surface configured to couple to the patient's tibia 52 at only one position. The bone-engaging surface 214 can be prepared based on any suitable imaging of the patient's tibia 52, such as three-dimensional imaging from a CAT scan or MRI, for example. Various tibial guides including exemplary patient-specific surfaces are described in the following applications, for example, which are incorporated herein by reference: U.S. patent application Ser. No. 11/756,057, filed on May 31, 2007; U.S. patent application Ser. No. 12/211,407, filed on Sep. 16, 2008; U.S. patent application Ser. No. 11/971,390, filed on Jan. 9, 2008; U.S. patent application Ser. No. 11/363,548, filed on Feb. 27, 2006; and U.S. patent application Ser. No. 12/025,414, filed on Feb. 4, 2008.

Figure 5:
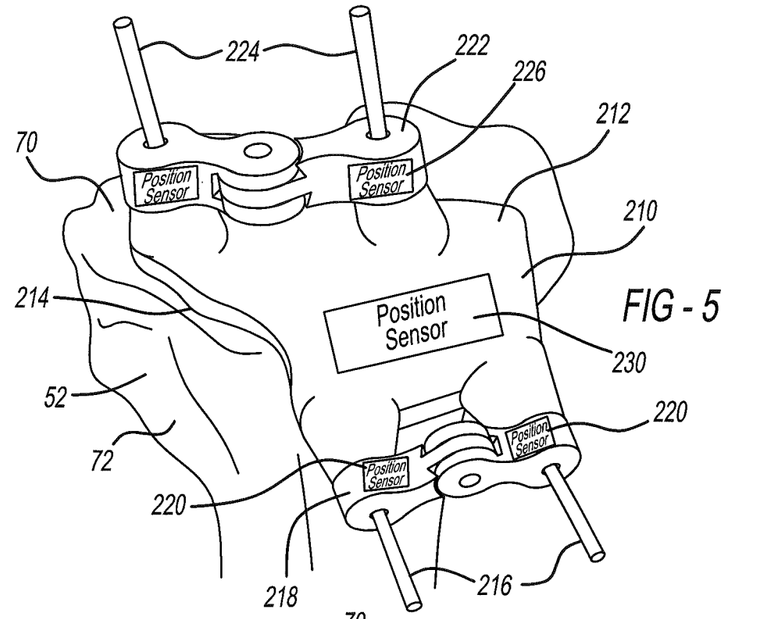
FIG. 5 is a perspective view of a tibial positioning guide according to the present teachings mounted to a tibia.

The tibial positioning guide 210 defines openings extending from the outer surface 212 to the bone-engaging surface 214, which are configured to receive and direct anterior pins 216 to the anterior surface 72 of the tibia 52. The anterior pins 216 can be any suitable pins for securing the tibial positioning guide 210 to the tibia 52 at the anterior surface 72 thereof. The anterior pins 216 can be guided through the tibial positioning guide 210 by anterior drill guide 218, which can be a femoral surgical device removably coupled to the tibial positioning guide 210, such as with a taper fit. The anterior drill guide 218 can include a position sensor 220, which can be any suitable position sensor configured to map location of the anterior drill guide 218 to a coordinate system, such as the mechanical axis A. Because the anterior drill guide 218 is fixably coupled to the tibial positioning guide 210 at a known orientation, mapping location of the anterior drill guide 218 to the mechanical axis A makes it possible to determine the location of the tibial positioning guide 210 relative to the longitudinal axis A.

The tibial positioning guide 210 further defines openings extending from the outer surface 212 to the bone-engaging surface 214 that are configured to receive and direct proximal pins 224 to the proximal surface 70 of the tibia 52. The proximal pins 224 can be any suitable pins configured to be driven into the tibia 52 in order to affix the tibial positioning guide 210 to the tibia 52. The proximal pins 224 can be guided through the tibial positioning guide 210 by proximal drill guide 222, which is configured to be coupled to the tibial positioning guide 210 at the guide holes accommodating the proximal pins 224 in any suitable manner, such as with a taper fit. The proximal drill guide 222 is a femoral surgical device, which can be fixably coupled to the tibial positioning guide 210.

The proximal drill guide 222 can include a position sensor 226. The position sensor 226 can be any suitable position sensor configured to permit mapping of the location of the proximal drill guide 222 relative to a coordinate axis, such as the mechanical axis A. Because the proximal drill guide 222 is rigidly coupled to the tibial positioning guide 210 at a known orientation, the position of the tibial positioning guide 210 with respect to the mechanical axis A can be determined based on location of the proximal drill guide 222 with respect to the mechanical axis A.

The tibial positioning guide 210 can further include a position sensor 230 mounted directly thereto. The position sensor 230 can be any suitable position sensor configured to map position of the tibial positioning guide 210 with respect to a coordinate system, such as the mechanical axis A. Because the position of the tibial positioning guide 210 will determine the position of the tibial implant, the position of the tibial implant relative to the mechanical axis A can be determined based on the position of the tibial positioning guide 210 relative to the mechanical axis A.

After the anterior pins 216 and the proximal pins 224 have been set, the proximal pins 224 can be removed and the tibial positioning guide 210 can be slid off of the anterior pins 216. With additional reference to FIG. 6, a tibial guide, such as a tibial cutting guide 250, can be slid onto the anterior pins 216 and positioned against the anterior surface 72 of the tibia 52. The tibial cutting guide 250 can be any suitable cutting guide, such as a cut block defining a guide slot 252 configured to direct a cutting instrument to the tibia 52 in order to make tibial cuts at proximal surface 70.

Figure 6:
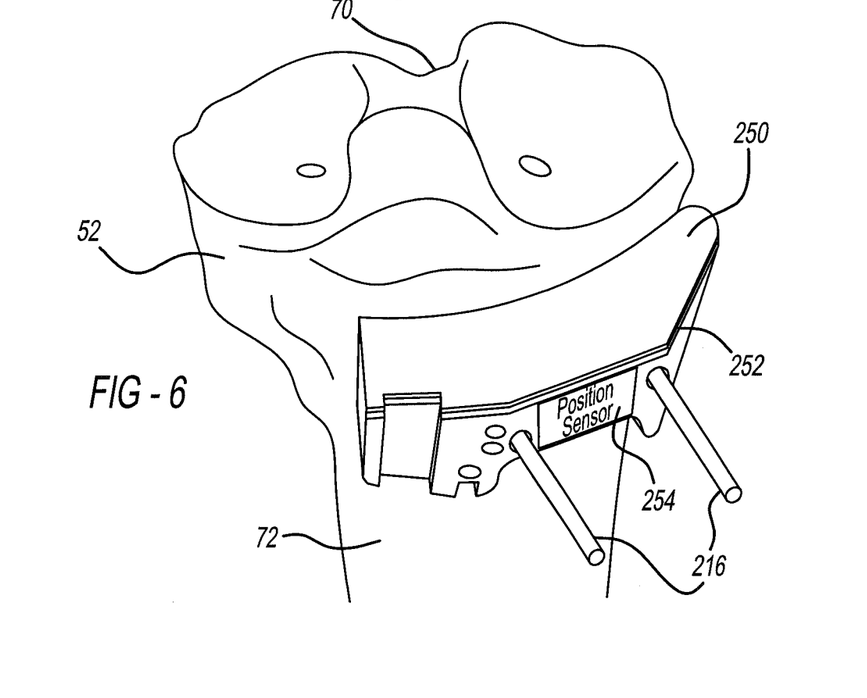
FIG. 6 is a perspective view of a tibial cutting guide according to the present teachings mounted to a tibia.

The tibial cutting guide 250 includes a position sensor 254 mounted thereto. The position sensor 254 can be any suitable position sensor configured to map location of the tibial cutting guide 250 to a coordinate system, such as the mechanical axis A. Because the position of the tibial cutting guide 250 with respect to the tibia 52 corresponds to the position and orientation of the tibial implant, the ultimate location of the tibial implant with respect to the mechanical axis A can be determined based on the position of the tibial cutting guide 250 with respect to the mechanical axis A.

After the tibial cutting guide 250 is mounted to the tibia 52, a distal tibial reference point is established at distal end 56 of the tibia 52 and the mechanical axis of the tibia 52 is determined. The position of the tibial cutting guide 250 can then be adjusted based on the mechanical axis of the tibia as well as the mechanical axis A in order to prepare the tibia 52 to receive an implant at optimal orientation relative to the femoral implant. The tibia 52 is prepared to receive an implant at block 18 of FIG. 1. The proximal surface 70 of the tibia 52 is resected using the tibial cutting guide 250 after the optimal position of the tibial cutting guide 250 is determined.

Figure 7:
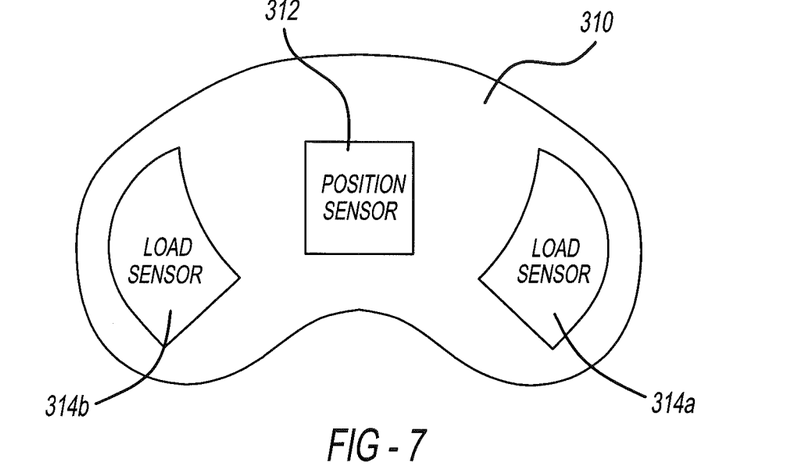
FIG. 7 is a top view (anterior view) of a tibial trial bearing according to the present teachings.

After the tibia 52 has been prepared to receive the tibia implant at block 18, a trial reduction can be performed at block 20 of the method 10 (FIG. 1) using a tibial surgical device, such as the tibial trial bearing 310 illustrated in FIG. 7, for example. The trial bearing 310 includes a position sensor 312, a first load sensor 314a, and a second load sensor 314b. The position sensor 312 can be any suitable sensor for mapping position of the trial bearing 310 relative to a coordinate system, such as mechanical axis A and/or a mechanical axis of the tibia. The load sensors 314a and 314b can be any suitable load sensing device for measuring load on the trial bearing 310 during trial reduction in order to facilitate positioning of a final tibial bearing implant. The first and second load sensors 314a and 314b can be arranged at any suitable position on the trial bearing 310. For example, load sensor 314a can be on a lateral side of the trial bearing 310, and load sensor 314b can be on a medial side of the trial bearing 310. Although the trial bearing 310 is illustrated as including two load sensors, any suitable number of load sensors can be provided. For example, one load sensor can be included, or more than two load sensors can be included.

At block 22 of the method 10 of FIG. 1, the resection of the tibia 52 can be validated using the load sensors 314a and 314b. At block 24, upper tibial rotation and long leg alignment can also be determined based on feedback from the load sensors 314a and 314b during trial reduction.

The trial bearing 310 can also be used to prepare the tibia 52 to receive a tibial implant at block 18 of the method 10 (FIG. 1). For example, the tibial cutting guide 250 can be connected to the trial bearing 310, and thus the position of the tibial cutting guide 250 can be determined based on the position of the position sensor 312 of the trial bearing 310, thereby eliminating the need for the position sensor 254 of the tibial cutting guide 250. The trial bearing 310 can be seated at the proximal surface 70 to align the tibial cutting guide 250 relative to the mechanical axis A and the tibial mechanical axis. After the optimal position of the tibial cutting guide 250 is achieved, the tibia 52 can be cut by directing any suitable cutting instrument through the guide slot 252. The position sensor 312 is optional and need not be included, such as when the trial bearing 310 is not used during preparation of the tibia 52 to receive an implant.

Use of each one of the position sensors 132, 134, 158, 220, 226, 230, 254, and 312, as well as the load sensors 314a and 314b may require activation and calibration prior to use. For example, if any one of the position sensors 132, 134, 158, 220, 226, 230, 254, and 312 include an accelerometer, then the accelerometer may have to be calibrated to identify where it is in space with respect to the coordinate system, such as the mechanical axis A or the tibial mechanical axis. The position sensors 132, 134, 158, 220, 226, 230, 254, and 312 can be any suitable sensors, such as electromagnetic sensors, RF sensors, micro-electromechanical sensor (MEMS), and accelerometers. The load sensors 314a and 314b can be any suitable type of load sensors, such as piezoresistive force sensors and MEMS. The position sensors 132, 134, 158, 220, 226, 230, 254 and the load sensors 314a and 314b can be configured to communicate with any suitable receiver or receivers located about the operating room.

The present teachings thus permit mapping of femoral and tibial guides to a single coordinate system, such as the mechanical axis A. The femoral guides, such as guides 110 and 150, can be mapped directly to the mechanical axis A using position sensor 134 for the guide 110 and position sensor 158 for the guide 150. The tibial guides, such as guides 210 and 250, can be mapped directly to the mechanical axis A using position sensor 230 for the guide 210 and position sensor 254 for the guide 250. The position sensor 312 of the trial bearing 310 can be used to map the guide 250 to the mechanical axis A as well, such as when the trial bearing 310 is coupled to the guide 250.

Other femoral surgical devices including position sensors can also be used to map the femoral guide 110 to the mechanical axis A, such as the drill guide 130 including position sensor 132. Other tibial surgical devices including position sensors can also be used to map the tibial guide 210 to the mechanical axis A, such as the anterior drill guide 218 including position sensor 220 or the proximal drill guide 222 including position sensor 226.

From the position of the femoral guides 110 and/or 150 relative to the mechanical axis A, the position of the final femoral implant relative to the mechanical axis A can be determined. From the position of the tibial guides 210 and/or 250, the position of the final tibial implant relative to the mechanical axis A can be determined. By varying the positions of the femoral guides 110/150 and/or the tibial guides 210/250 relative to the mechanical axis A, optimal orientation of the femoral and tibial implants relative to the mechanical axis A can be achieved.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for preparing a femur and a tibia to receive implants comprising:
    mapping location of a femoral guide to a leg mechanical axis using a femoral position sensor mounted to at least one of the femoral guide or another femoral surgical device during preparation of the femur to receive a femoral implant;
    determining a tibial mechanical axis; and
    mapping location of a tibial guide to the leg mechanical axis and the tibial mechanical axis using a tibial position sensor mounted to at least one of the tibial guide or another tibial surgical device during preparation of the tibia to receive a tibial implant.

2. The method of claim 1, further comprising mounting the femoral guide to the femur such that a patient-specific bone-engaging surface of the femoral guide mates with the femur.

3. The method of claim 1, wherein mapping location of the femoral guide and the tibial guide to the leg mechanical axis includes mapping location of the femoral guide and the tibial guide to a mechanical axis of a leg including the knee joint.

4. The method of claim 1; wherein the femoral guide includes at least one of a cutting guide, a generic femoral positioning guide, or a patient-specific femoral positioning guide including a patient-specific bone-engaging surface configured to mate with the femur at only a single position; and
    wherein the tibial guide includes at least one of a cutting guide, a generic tibial positioning guide, or a patient-specific tibial positioning guide including a patient-specific bone-engaging surface configured to mate with the tibia at only a single position.

5. The method of claim 1, further comprising at least one of the following: coupling the other femoral surgical device to the femoral guide; or coupling the other tibial surgical device to the tibial guide.

6. The method of claim 1, further comprising mapping location of the tibial guide to the leg mechanical axis with the tibial position sensor mounted to a trial tibial bearing coupled to the tibial guide, the trial tibial bearing constituting the other tibial surgical device.

7. The method of claim 1, further comprising performing a trial joint reduction using a load sensor included with a trial tibial bearing constituting the other tibial surgical device.

8. The method of claim 1, further comprising performing a trial joint reduction using a load sensor coupled to the tibial guide.

9. The method of claim 1, further comprising determining a tibial mechanical axis, positioning the tibial guide based on location of the tibial mechanical axis, and resecting the tibia using the tibial guide.

10. The method of claim 9, further comprising validating the resection using a load sensor, and determining both optimal tibial rotation and long leg alignment.

11. A method for preparing a femur and a tibia to receive implants comprising:
    mapping location of a femoral guide to a leg mechanical axis using a femoral position sensor mounted to at least one of the femoral guide or another femoral surgical device during preparation of the femur to receive a femoral implant at a position relative to the mechanical axis;
    determining a tibial mechanical axis; and
    mounting a tibial guide to the tibia relative to the leg mechanical axis and the tibial mechanical axis using a tibial position sensor mounted to at least one of the tibial resection guide or another tibial surgical device during preparation of the tibia to receive a tibial implant.

12. The method of claim 11, further comprising performing a knee joint trial reduction using a tibial trial bearing including a load sensor.

13. The method of claim 11, further comprising performing a knee joint trial reduction using a tibial trial bearing including a load sensor and the tibial position sensor.

14. The method of claim 11, further comprising at least one of the following: coupling the other femoral surgical device to the femoral guide; or coupling the other tibial surgical device to the tibial guide;
    wherein the femoral guide includes at least one of a cutting guide, a generic femoral positioning guide, or a patient-specific femoral positioning guide including a patient-specific bone-engaging surface configured to mate with the femur only at a single position; and
    wherein the tibial guide includes at least one of a cutting guide, a generic tibial positioning guide, or a patient-specific tibial positioning guide including a patient-specific bone-engaging surface configured to mate with the tibia only at only a single position.

15. A system for preparing a femur and a tibia to receive implants comprising:
    a femoral position sensor configured to map location of a femoral guide to a leg mechanical axis, the femoral position sensor mounted to at least one of the femoral guide or another femoral surgical device for preparing the femur to receive a femoral implant; and
    a tibial position sensor configured to map location of a tibial guide to the leg mechanical axis and a tibial mechanical axis, the tibial position sensor mounted to at least one of the tibial guide or another tibial surgical device for preparing the tibia to receive a tibial implant.

16. The kit of claim 15, wherein the femoral guide is at least one of a cutting guide, a generic femoral positioning guide, or a patient-specific femoral positioning guide including a patient-specific bone-engaging surface configured to mate with the femur at only a single position.

17. The system of claim 15, wherein the other femoral surgical device is configured to couple with the femoral guide.

18. The system of claim 15, wherein the tibial guide is at least one of a cutting guide, a generic tibial positioning guide, or a patient-specific tibial positioning guide including a patient-specific bone-engaging surface configured to mate with the tibia at only a single position.

19. The system of claim 15, wherein the other tibial surgical device is configured to couple with the tibial guide.

20. The system of claim 19, wherein the other tibial surgical device is at least one of a tibial trial bearing without a load sensor, a tibial trial bearing including a load sensor, or a drill guide.

* * * * *

UNITED STATES PATENT AND TRADEMARK OFFICE
CERTIFICATE OF CORRECTION

PATENT NO. : 9,463,030 B2  
APPLICATION NO. : 14/036124  
DATED : October 11, 2016  
INVENTOR(S) : Brian Uthgenannt Page 1 of 1

It is certified that error appears in the above-identified patent and that said Letters Patent is hereby corrected as shown below:

In the Claims

In Column 7, Line 53, in Claim 4, delete "claim 1;" and insert --claim 1,--, therefor Signed and Sealed this  
Fifth Day of June, 2018

Andrei Iancu  
*Director of the United States Patent and Trademark Office*